(12) United States Patent
Danna et al.

(10) Patent No.: US 12,193,640 B2
(45) Date of Patent: Jan. 14, 2025

(54) SYSTEMS AND METHODS FOR ROBOTIC BRONCHOSCOPY NAVIGATION

(71) Applicant: Noah Medical Corporation, Redwood City, CA (US)

(72) Inventors: Kyle Ross Danna, Scotts Valley, CA (US); Jian Zhang, San Mateo, CA (US); Carol Kayee Hung, Palo Alto, CA (US); Michael J. Shawver, Mill Valley, CA (US); Piotr Robert Slawinski, South San Francisco, CA (US); Hendrik Thompson, San Francisco, CA (US); Liya K. Abraha, San Francisco, CA (US)

(73) Assignee: Noah Medical Corporation, Redwood City, CA (US)

( * ) Notice: Subject to any disclaimer, the term of this patent is extended or adjusted under 35 U.S.C. 154(b) by 410 days.

(21) Appl. No.: 17/838,857

(22) Filed: Jun. 13, 2022

(65) Prior Publication Data
US 2022/0361736 A1 Nov. 17, 2022

Related U.S. Application Data

(63) Continuation of application No. PCT/US2020/066067, filed on Dec. 18, 2020.
(Continued)

(51) Int. Cl.
| | |
|---|---|
| *A61B 1/00* | (2006.01) |
| *A61B 34/10* | (2016.01) |
| *A61B 34/20* | (2016.01) |
| *A61B 34/30* | (2016.01) |
| *G06F 18/2413* | (2023.01) |

(52) U.S. Cl.
CPC ...... *A61B 1/00147* (2013.01); *A61B 1/00158* (2013.01); *A61B 34/10* (2016.02);
(Continued)

(58) Field of Classification Search
CPC . A61B 1/00147; A61B 1/00158; A61B 34/10; A61B 34/20; A61B 34/30;
(Continued)

(56) References Cited

U.S. PATENT DOCUMENTS

| 2007/0167700 A1* | 7/2007 | Rahn | A61B 90/36 |
| | | | 600/407 |
| 2008/0049994 A1* | 2/2008 | Rognin | G06T 7/35 |
| | | | 382/128 |

(Continued)

FOREIGN PATENT DOCUMENTS

WO WO-2021127475 A1 6/2021

OTHER PUBLICATIONS

Elseberg et al. Comparison of nearest-neighbor-search strategies and implementations for efficient shape registration. Journal of Software Engineering for Robotics. Mar. 2023, 2-12.
(Continued)

*Primary Examiner* — John P Leubecker
*Assistant Examiner* — Jae Woo
(74) *Attorney, Agent, or Firm* — Wilson Sonsini Goodrich & Rosati

(57) ABSTRACT

A method is provided for auto registration for a robotic endoscopic apparatus. The method comprises: (a) generate a first transformation between an orientation of the robotic endoscopic apparatus and an orientation of a location sensor based at least in part on a first set of sensor data collected using the location sensor; (b) generating a second transformation between a coordinate frame of the robotic endoscopic apparatus and a coordinate frame of a model representing an anatomical luminal network based at least in part on the first transformation and a second set of sensor data; and (c) updating, based at least in part on a third set of sensor data, the second transformation using an updating algorithm.

16 Claims, 11 Drawing Sheets

Related U.S. Application Data

(60) Provisional application No. 63/091,283, filed on Oct. 13, 2020, provisional application No. 62/950,740, filed on Dec. 19, 2019.

(52) U.S. Cl.
CPC .............. *A61B 34/20* (2016.02); *A61B 34/30* (2016.02); *G06F 18/24147* (2023.01); *A61B 2034/105* (2016.02); *A61B 2034/107* (2016.02); *A61B 2034/2051* (2016.02); *A61B 2034/301* (2016.02); *A61B 2034/303* (2016.02)

(58) Field of Classification Search
CPC ........ A61B 2034/105; A61B 2034/107; A61B 2034/2051; A61B 2034/301; A61B 2034/303; G06F 18/24147
See application file for complete search history.

(56) References Cited

U.S. PATENT DOCUMENTS

| | | | | |
|---|---|---|---|---|
| 2010/0002955 | A1* | 1/2010 | George | G06T 11/006 382/280 |
| 2015/0305612 | A1* | 10/2015 | Hunter | A61B 1/00057 600/109 |
| 2017/0035380 | A1 | 2/2017 | Barak et al. | |
| 2017/0172457 | A1* | 6/2017 | Govari | A61M 25/0127 |
| 2018/0279852 | A1 | 10/2018 | Rafii-Tari et al. | |
| 2019/0313910 | A1 | 10/2019 | Vignon et al. | |
| 2019/0320878 | A1 | 10/2019 | Duindam et al. | |
| 2019/0340800 | A1 | 11/2019 | Merlet et al. | |
| 2019/0340838 | A1 | 11/2019 | Gluhovsky et al. | |
| 2019/0365209 | A1* | 12/2019 | Ye | A61B 34/30 |
| 2022/0296302 | A1* | 9/2022 | Bleunven | A61B 34/30 |

OTHER PUBLICATIONS

PCT/US2020/066067 Search Report & Written Opinion dated Mar. 10, 2021.
Pomerleau et al. A Review of Point Cloud Registration Algorithms for Mobile Robotics. Foundations and Trends in Robotics, Now Publishers, 2015, 4(1), pp. 1-104.
EP20901611.2 Extended European Search Report dated Nov. 23, 2023.

* cited by examiner

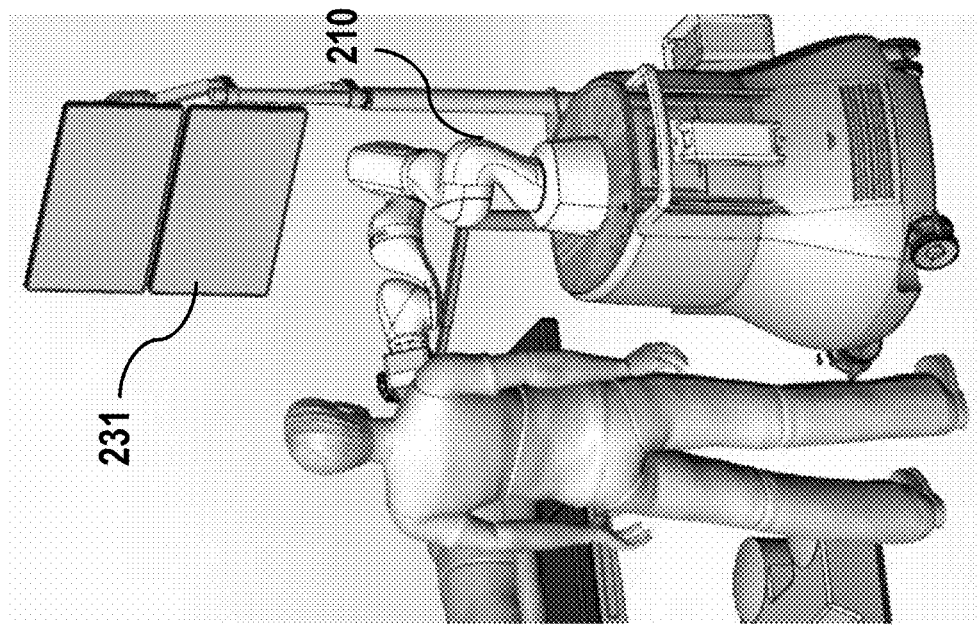
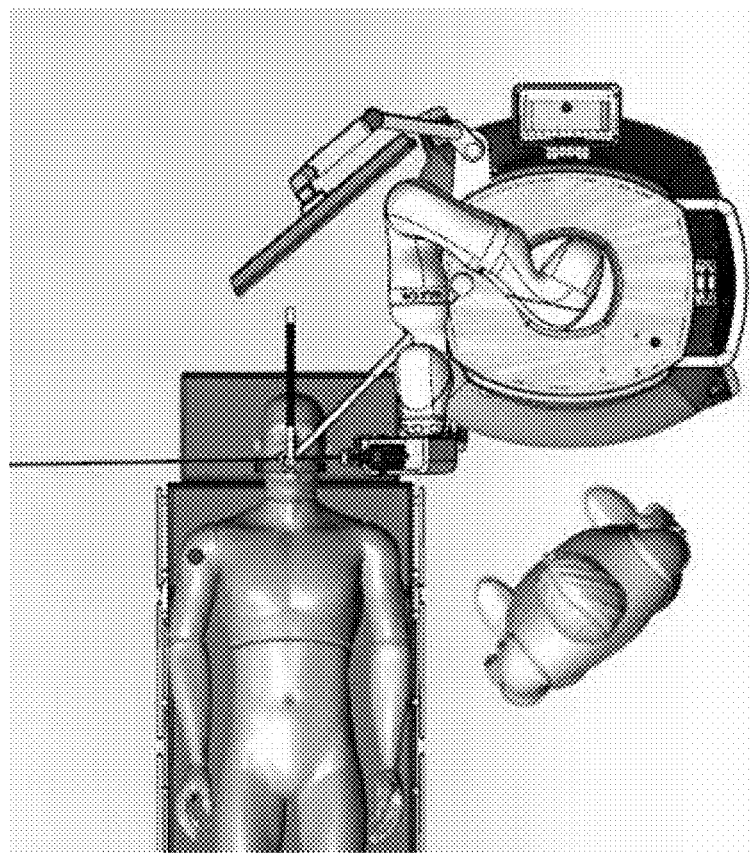
FIG. 2B

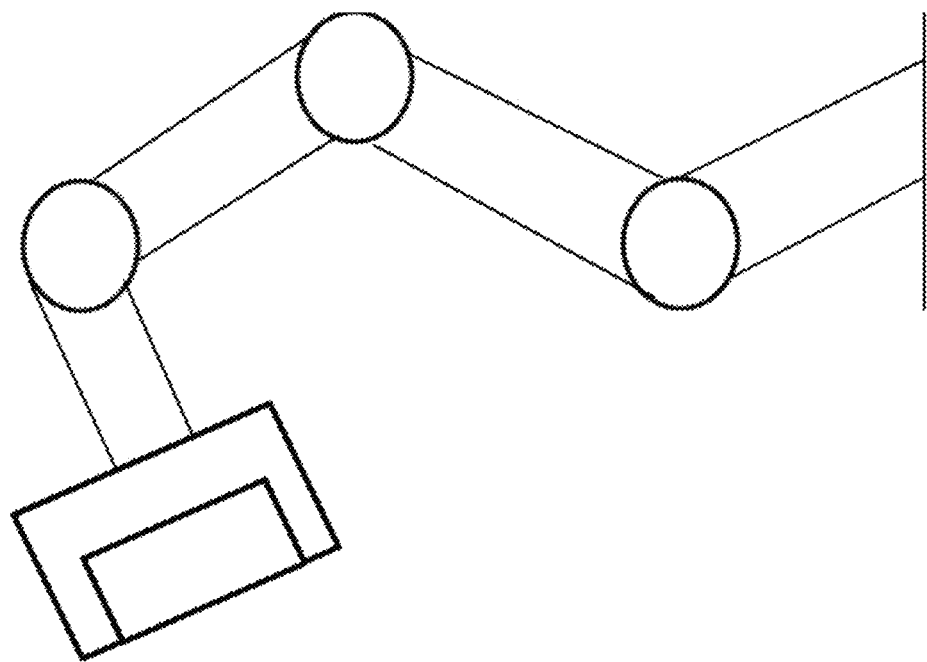
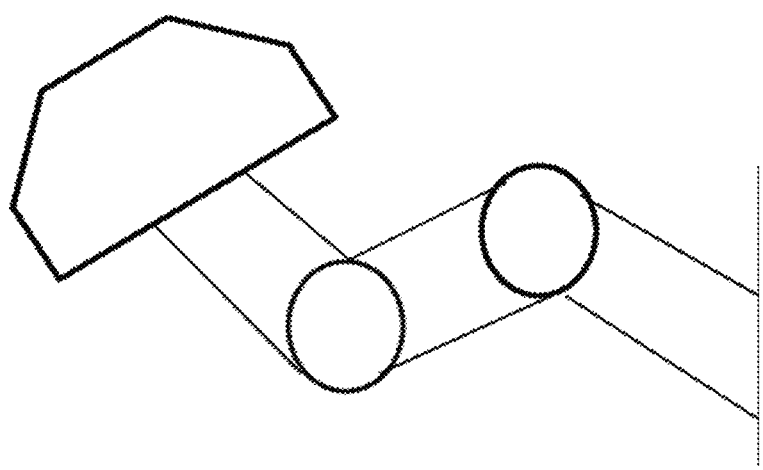
FIG. 6

SYSTEMS AND METHODS FOR ROBOTIC BRONCHOSCOPY NAVIGATION

REFERENCE

This application is a Continuation application of PCT/US2020/066067, filed Dec. 18, 2020, which claims priority to U.S. Provisional Patent Application No. 62/950,740, filed Dec. 19, 2019, and U.S. Provisional Patent Application No. 63/091,283, filed on Oct. 13, 2020, each of which is entirely incorporated herein by reference.

BACKGROUND OF THE INVENTION

Early diagnosis of lung cancer is critical. The five-year survival rate of lung cancer is around 18% which is significantly lower than next three most prevalent cancers: breast (90%), colorectal (65%), and prostate (99%). A total of 142,000 deaths were recorded in 2018 due to lung cancer.

In general, a typical lung cancer diagnosis and surgical treatment process can vary drastically, depending on the techniques used by healthcare providers, the clinical protocols, and the clinical sites. The inconsistent process can delay the diagnosis of the cancer as well as imposing a high cost on the patient and the health care system.

These medical procedures such as endoscopy (e.g., bronchoscopy) may involve accessing and visualizing the inside of a patient's lumen (e.g., airways) for diagnostic and/or therapeutic purposes. During a procedure, a flexible tubular tool such as, for example, an endoscope, may be inserted into the patient's body and an instrument can be passed through the endoscope to a tissue site identified for diagnosis and/or treatment.

SUMMARY OF THE INVENTION

Endoscopes comprise vast applications in diagnosis and treatment of various conditions, such as medical conditions (e.g., early lung cancer diagnosis and treatment). An endoscopy navigation system may use different sensing modalities (e.g., camera imaging data, electromagnetic (EM) position data, robotic position data, etc.) modeled, for example, through adaptively-adjusted probabilities. The navigation approach may depend on an initial estimate of where the tip of the endoscope is with respect to the airway to begin tracking the tip of the endoscope. Some endoscopy techniques may involve a three-dimensional (3D) model of a patient's anatomy, and guide navigation using an EM field and position sensors. Prior to a procedure, the precise alignment (e.g., registration) between the virtual space of the 3D model, the physical space of the patient's anatomy represented by the 3D model, and the EM field may be unknown. As such, prior to generating a registration, endoscope positions within the patient's anatomy cannot be mapped with precision to corresponding locations within the 3D model.

Navigation of the bronchoscope can be challenging due to inaccurate registration. In particular, current registration procedure can be time consuming and clunky, or producing inconsistent results affected by human input. Current registration procedure may involve generating an estimated initial registration then refining or updating the initial registration during a procedure. For example, current registration method may compensate for changes to the navigation system by sampling from real-time sensor data. However, as the device is driven during a long operation and as more incoming data being collected by the system, the computation time increases drastically. Furthermore, the current registration procedure may not have a satisfying online update capability leading to compromised registration accuracy. For instance, the current registration procedure may not be capable of adapting to a local change which may result in an inaccurate registration algorithm. For example, sampled datasets are usually used to make a global update to the registration algorithm (e.g., transformation) which does not accurately reflect a local change (e.g., due to a local, small mechanical deflection). In another example, the current registration algorithm may have a poor transformation accuracy when the endoscope does not travel along a pre-determined path (e.g., take cut of the centerline of the airway, etc.).

Recognized herein is a need for a minimally invasive system that allows for performing surgical procedures or diagnostic operations with improved reliability and cost-efficiency. Another need recognized herein is for an improved registration algorithm that can increase registration accuracy while reducing the registration time. The present disclosure provides systems and methods allowing for standardized early lung cancer diagnosis and treatment at reduced cost. The present disclosure provides accessible, more cost-effective methods and systems for early stage diagnosis and treatment of cancers. In some embodiments of the invention, at least a portion of the robotic bronchoscopy system is disposable. For instance, the catheter portion may be designed to be disposable at low cost while preserving the surgical performance capability and functionality. Moreover, the provided robotic bronchoscopy system is designed with capability to access hard-to-reach tissues such as bronchus, lung, without introducing extra cost.

The adaptive navigation algorithm may be capable of identifying a registration or mapping between the coordinate frame of the 3D model (e.g., a coordinate frame of the CT scanner used to generate the model) and the coordinate frame of the EM field (e.g., of the EM field generator) with on-the-fly updates capability.

In an aspect, a method for navigating a robotic endoscopic apparatus is provided. The method comprises: (a) generate a first transformation between an orientation of the robotic endoscopic apparatus and an orientation of a location sensor based at least in part on a first set of sensor data collected using the location sensor; (b) generating a second transformation between a coordinate frame of the robotic endoscopic apparatus and a coordinate frame of a model representing an anatomical luminal network based at least in part on the first transformation and a second set of sensor data; and (c) updating, based at least in part on a third set of sensor data, the second transformation using an updating algorithm.

In some embodiments, the updating algorithm comprises a fast interval recalculation operation and a slow interval recalculation operation. In some cases, the fast interval recalculation operation comprises (i) calculating a first set of associations using a subset of data sampled from the third set of sensor data and (ii) combining the first set of associations with a second set of associations calculated for generating the second transformation in (b). For example, the method further comprises calculating a point cloud using the combined first and second set of associations. In some cases, the slow interval recalculation operation comprises a nearest neighbor algorithm. In some cases, the slow interval recalculation operation comprises updating the second transformation using only the third set of sensor data.

In some embodiments, the location sensor is an electromagnetic sensor. In some embodiments, the coordinate frame of the model representing an anatomical luminal network is generated using a pre-operative imaging system.

In some embodiments, the robotic endoscopic apparatus comprises a disposable catheter assembly. In some embodiments, the location sensor is located at a distal tip of the robotic endoscopic apparatus.

In another aspect, a system for navigating a robotic endoscopic apparatus is provided. The system comprises: a location sensor located at a distal end of the robotic endoscopic apparatus; and one or more processors in communication with the location sensor and the robotic endoscopic apparatus and configured to execute a set of instructions to cause the system to: (a) generate a first transformation between an orientation of the robotic endoscopic apparatus and an orientation of the location sensor based at least in part on a first set of sensor data collected using the location sensor; (b) generate a second transformation between a coordinate frame of the robotic endoscopic apparatus and a coordinate frame of a model representing an anatomical luminal network based at least in part on the first transformation and a second set of sensor data; and (c) update, based at least in part on a third set of sensor data, the second transformation using an updating algorithm.

In some embodiments, the updating algorithm comprises a fast interval recalculation operation and a slow interval recalculation operation. In some cases, the fast interval recalculation operation comprises (i) calculating a first set of associations using a subset of data sampled from the third set of sensor data and (ii) combining the first set of associations with a second set of associations calculated for generating the second transformation in (b). For example, the fast interval recalculation operation further comprises calculating a point cloud using the combined first and second set of associations. In some cases, the slow interval recalculation operation comprises a nearest neighbor algorithm. In some cases, the slow interval recalculation operation comprises updating the second transformation using only the third set of sensor data.

In some embodiments, the location sensor is an electromagnetic sensor. In some embodiments, the coordinate frame of the model representing the anatomical luminal network is generated using a pre-operative imaging system. In some embodiments, the robotic endoscopic apparatus comprises a disposable catheter assembly.

According to some aspects of the disclosure, a robotic endoscopic apparatus is provided. The apparatus may include a disposable elongate member comprising a proximal end and a distal end and the proximal end is removably attached to a robotic arm. The distal end comprises a plurality of pull wires and the pull wires integrated with the walls of the elongate member. The elongate member may also be referred to as bronchoscope, catheter which can be used interchangeably throughout the specification.

In another aspect of the present disclosure, an improved registration algorithm or navigation method is provided. The registration algorithm may allow for automatic registration with minimal user interaction, and online registration updates which beneficially increase registration accuracy. It should be noted that the provided robotic systems and/or registration algorithm can be used in various minimally invasive surgical procedures that involve various types of tissue including heart, bladder and lung tissue and others.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 2B shows different views of an example robotic bronchoscopy system, in accordance with some embodiments of the invention.

FIG. 6 shows an example portable robotic cone beam CT.

DETAILED DESCRIPTION OF THE INVENTION

Figure 1:
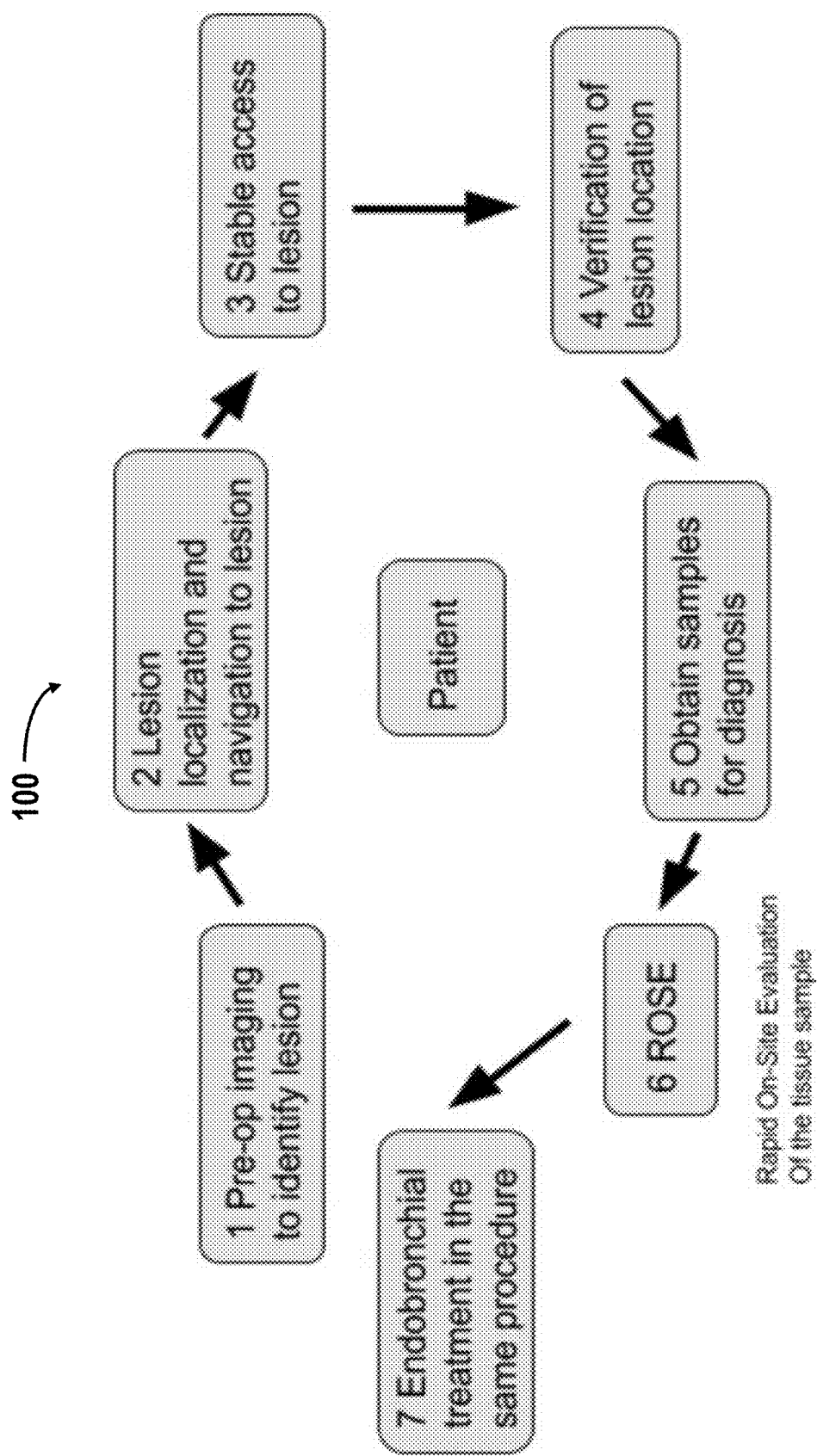
FIG. 1 shows an example workflow of standardized lung cancer diagnosis enabled by the robotic bronchoscopy system described herein.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

While exemplary embodiments will be primarily directed at a bronchoscope, one of skill in the art will appreciate that this is not intended to be limiting, and the devices described herein may be used for other therapeutic or diagnostic procedures and in other anatomical regions of a patient's body such as a digestive system, including but not limited to the esophagus, liver, stomach, colon, urinary tract, or a respiratory system, including but not limited to the bronchus, the lung, and various others. The registration method/algorithm herein can be used for aligning a medical device's coordinates frame with the coordinate frame of a 3D model (e.g., airway model or patient coordinate frame generated by a CT scanner) regardless the types of devices or operations to be performed.

The embodiments disclosed herein can be combined in one or more of many ways to provide improved diagnosis and therapy to a patient. The disclosed embodiments can be combined with existing methods and apparatus to provide improved treatment, such as combination with known methods of pulmonary diagnosis, surgery and surgery of other tissues and organs, for example. It is to be understood that any one or more of the structures and steps as described herein can be combined with any one or more additional structures and steps of the methods and apparatus as described herein, the drawings and supporting text provide descriptions in accordance with embodiments.

Although the treatment planning and definition of diagnosis or surgical procedures as described herein are presented in the context of pulmonary diagnosis or surgery, the methods and apparatus as described herein can be used to treat any tissue of the body and any organ and vessel of the body such as brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone and the like, as well as body lumens and passages such as the sinuses, ureter, colon, esophagus, lung passages, blood vessels and throat.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein a processor encompasses one or more processors, for example a single processor, or a plurality of processors of a distributed processing system for example. A controller or processor as described herein generally comprises a tangible medium to store instructions to implement steps of a process, and the processor may comprise one or more of a central processing unit, programmable array logic, gate array logic, or a field programmable gate array, for example. In some cases, the one or more processors may be a programmable processor (e.g., a central processing unit (CPU) or a microcontroller), digital signal processors (DSPs), a field programmable gate array (FPGA) and/or one or more Advanced RISC Machine (ARM) processors. In some cases, the one or more processors may be operatively coupled to a non-transitory computer readable medium. The non-transitory computer readable medium can store logic, code, and/or program instructions executable by the one or more processors unit for performing one or more steps. The non-transitory computer readable medium can include one or more memory units (e.g., removable media or external storage such as an SD card or random access memory (RAM)). One or more methods or operations disclosed herein can be implemented in hardware components or combinations of hardware and software such as, for example, ASICs, special purpose computers, or general purpose computers.

As used herein, the terms distal and proximal may generally refer to locations referenced from the apparatus, and can be opposite of anatomical references. For example, a distal location of a bronchoscope or catheter may correspond to a proximal location of an elongate member of the patient, and a proximal location of the bronchoscope or catheter may correspond to a distal location of the elongate member of the patient.

A system as described herein, includes an elongate portion or elongate member such as a catheter. The terms "elongate member", "catheter", "bronchoscope" are used interchangeably throughout the specification unless contexts suggest otherwise. The elongate member can be placed directly into the body lumen or a body cavity. In some embodiments, the system may further include a support apparatus such as a robotic manipulator (e.g., robotic arm) to drive, support, position or control the movements and/or operation of the elongate member. Alternatively or in addition to, the support apparatus may be a hand-held device or other control devices that may or may not include a robotic system. In some embodiments, the system may further include peripheral devices and subsystems such as imaging systems that would assist and/or facilitate the navigation of the elongate member to the target site in the body of a subject. Such navigation may require a registration process which will be described later herein.

In some embodiments of the present disclosure, a robotic bronchoscopy system is provided for performing surgical operations or diagnosis with improved performance at low cost. For example, the robotic bronchoscopy system may comprise a steerable catheter that can be entirely disposable. This may beneficially reduce the requirement of sterilization which can be high in cost or difficult to operate, yet the sterilization or sanitization may not be effective. Moreover, one challenge in bronchoscopy is reaching the upper lobe of the lung while navigating through the airways. In some cases, the provided robotic bronchoscopy system may be designed with capability to navigate through the airway having a small bending curvature in an autonomous or semi-autonomous manner. The autonomous or semi-autonomous navigation may require a registration process as described later herein. Alternatively, the robotic bronchoscopy system may be navigated by an operator through a control system with vision guidance.

A typical lung cancer diagnosis and surgical treatment process can vary drastically, depending on the techniques used by healthcare providers, the clinical protocols, and the clinical sites. The inconsistent processes may cause delay to diagnose lung cancers in early stage, high cost of healthcare system and the patients to diagnose and treat lung cancers, and high risk of clinical and procedural complications. The provided robotic bronchoscopy system may allow for standardized early lung cancer diagnosis and treatment. FIG. 1 shows an example workflow 100 of standardized lung cancer diagnosis enabled by the robotic bronchoscopy system described herein.

As illustrated in FIG. 1, pre-operative imaging may be performed to identify lesions. Any suitable imaging modalities such as magnetic resonance (MR), positron emission tomography (PET), X-ray, computed tomography (CT) and ultrasound may be used to identify lesions or regions of interest. For instance, a patient with suspect lung cancer may be administered a pre-operative CT scan and suspect lung nodules may be identified in the CT images. The pre-operative imaging process can be performed prior to the bronchoscopy.

Next, the CT images may be analyzed to generate a map to guide the navigation of the robotic bronchoscope at the time of bronchoscopy. For example, the lesion or the region of interest (ROI) may be segmented on the images. When the lung is under imaging, the passage or pathway to the lesion may be highlighted on the reconstructed images for planning a navigation path. The reconstructed images may guide the navigation of the robotic bronchoscope to the target tissue or target site. In some cases, the navigation path may be pre-planned using 3D image data. For instance, the catheter may be advanced toward the target site under a robotic control of the robotic bronchoscope system. The catheter may be steered or advanced towards the target site in a manual manner, an autonomous manner, or a semi-autonomous manner. In an example, the movement of the catheter may be image guided such that the insertion and/or steering direction may be controlled automatically.

In some cases, the lesion location in the pre-operative imaging may not be accurate due to patient motion or body divergence. In such cases, the lesion location may be verified prior to a surgical procedure (e.g., biopsy or treatment). The accurate location of the lesion may be verified or updated with aid of the robotic bronchoscopy system. For instance, the bronchoscopy system may provide interface to imaging modalities such as fluoroscopy to provide in vivo real-time imaging of the target site and the surrounding areas to locate the lesion. In an example, a C arm or O arm fluoroscopic imaging system may be used to generate a tomosynthesis image for verifying or updating the location of the lesion. Proceeding to the surgical procedures such as biopsy, various surgical tools such as biopsy tools, brushes or forceps may be inserted into the working channel of the catheter to perform biopsy or other surgical procedures manually or automatically.

Next, samples of the lesion or any other target tissue may be obtained by the tools inserted through the working channel of the catheter. The system allows for camera visualization to be maintained throughout the procedure, including during the insertion of tools through the working channel. In some cases, the tissue sample may be rapidly evaluated on-site by a rapid on-site evaluation process to determine whether repetition of the tissue sampling is needed, or to decide further action. In some cases, the rapid on-site evaluation process may also provide a quick analysis on the tissue sample to determine the following surgical treatment. For instance, if the tissue sample is determined to be malignant as a result of the rapid on-site evaluation process, a manual or robotic treatment instrument may be inserted through the working channel of the robotic bronchoscope and perform endobronchial treatment of the lung cancer. This beneficially allows for diagnosis and treatment being performed in one session thereby providing targeted, painless, and fast treatment of early stage lung cancer.

Figure 2A:
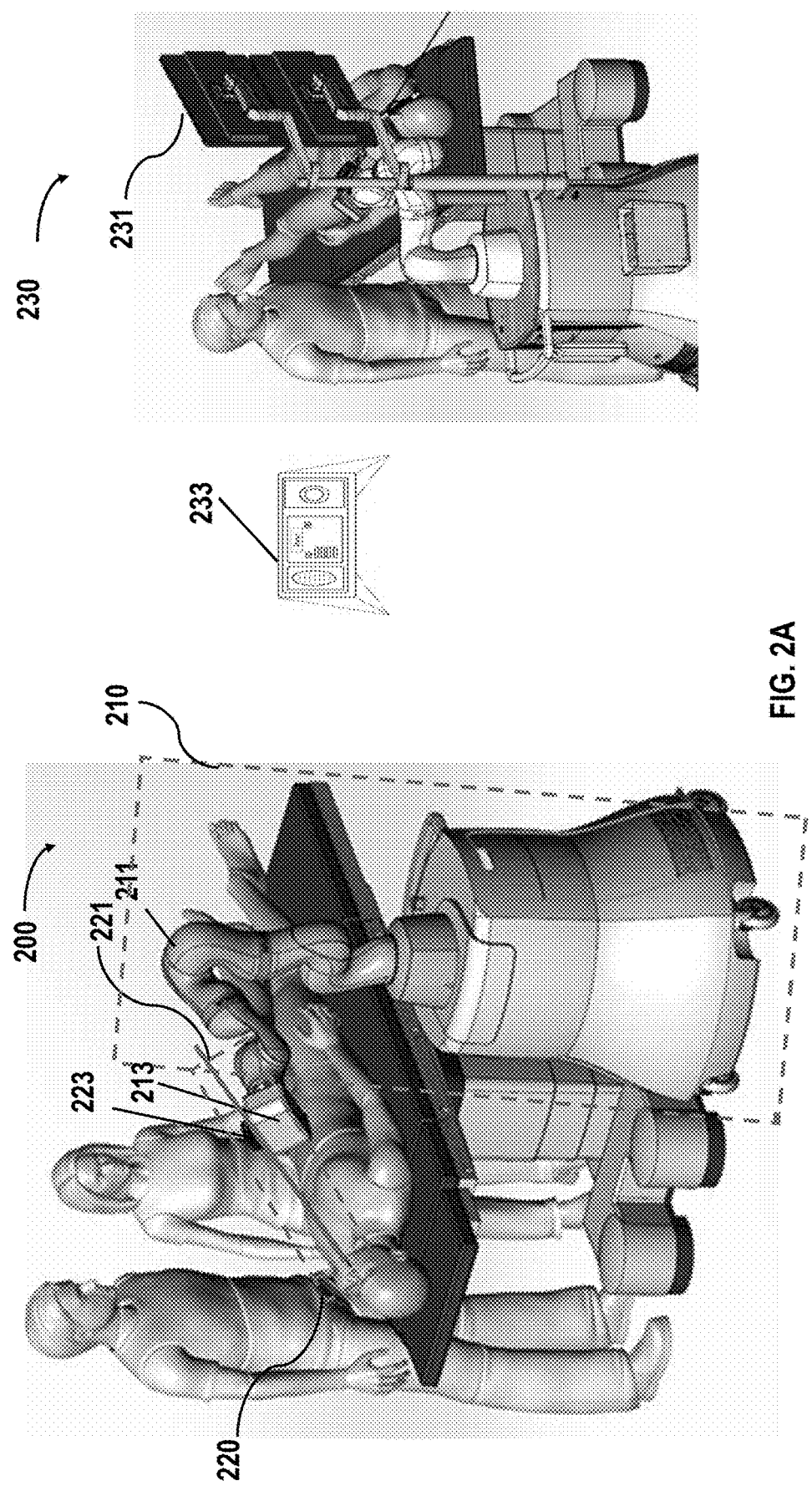
FIG. 2A shows examples of robotic bronchoscopy systems, in accordance with some embodiments of the invention.

FIGS. 2A and 2B show examples of robotic bronchoscopy system 200, 230, in accordance with some embodiments of the invention. As shown in FIG. 2A, the robotic bronchoscopy system 200 may comprise a steerable catheter assembly 220 and a robotic support system 210, for supporting or carrying the steerable catheter assembly. The steerable catheter assembly can be a bronchoscope. In some embodiments, the steerable catheter assembly may be a single-use robotic bronchoscope. In some embodiments, the robotic bronchoscopy system 200 may comprise an instrument driving mechanism 213 that is attached to the arm of the robotic support system. The instrument driving mechanism may be provided by any suitable controller device (e.g., hand-held controller) that may or may not include a robotic system. The instrument driving mechanism may provide mechanical and electrical interface to the steerable catheter assembly 220. The mechanical interface may allow the steerable catheter assembly 220 to be releasably coupled to the instrument driving mechanism. For instance, a handle portion of the steerable catheter assembly can be attached to the instrument driving mechanism via quick install/release means, such as magnets, spring-loaded levels and the like. In some cases, the steerable catheter assembly may be coupled to or released from the instrument driving mechanism manually without using a tool.

The steerable catheter assembly 220 may comprise a handle portion 223 that may include components configured to processing image data, provide power, or establish communication with other external devices. For instance, the handle portion 223 may include a circuitry and communication elements that enables electrical communication between the steerable catheter assembly 220 and the instrument driving mechanism 213, and any other external system or devices. In another example, the handle portion 223 may comprise circuitry elements such as power sources for powering the electronics (e.g. camera and LED lights) of the endoscope. In some cases, the handle portion may be in electrical communication with the instrument driving mechanism 213 via an electrical interface (e.g., printed circuit board) so that image/video data and/or sensor data can be received by the communication module of the instrument driving mechanism and may be transmitted to other external devices/systems. Alternatively or in addition to, the instrument driving mechanism 213 may provide a mechanical interface only. The handle portion may be in electrical communication with a modular wireless communication device or any other user device (e.g., portable/hand-held device or controller) for transmitting sensor data and/or receiving control signals. Details about the handle portion are described later herein.

The steerable catheter assembly 220 may comprise a flexible elongate member 211 that is coupled to the handle portion. In some embodiments, the flexible elongate member may comprise a shaft, steerable tip and a steerable section. The steerable catheter assembly may be a single use robotic bronchoscope. In some cases, only the elongate member may be disposable. In some cases, at least a portion of the elongate member (e.g., shaft, steerable tip, etc) may be disposable. In some cases, the entire steerable catheter assembly 220 including the handle portion and the elongate member can be disposable. The flexible elongate member and the handle portion are designed such that the entire steerable catheter assembly can be disposed of at low cost. Details about the flexible elongate member and the steerable catheter assembly are described later herein.

In some embodiments, the provided bronchoscope system may also comprise a user interface. As illustrated in the example system 230, the bronchoscope system may include a treatment interface module 231 (user console side) and/or a treatment control module 233 (patient and robot side). The treatment interface module may allow an operator or user to interact with the bronchoscope during surgical procedures. In some embodiments, the treatment control module 233 may be a hand-held controller. The treatment control module may, in some cases, comprise a proprietary user input device and one or more add-on elements removably coupled to an existing user device to improve user input experience. For instance, physical trackball or roller can replace or supplement the function of at least one of the virtual graphical element (e.g., navigational arrow displayed on touchpad) displayed on a graphical user interface (GUI) by giving it similar functionality to the graphical element which it replaces. Examples of user devices may include, but are not limited to, mobile devices, smartphones/cellphones, tablets, personal digital assistants (PDAs), laptop or notebook computers, desktop computers, media content players, and the like. Details about the user interface device and user console are described later herein.

FIG. 2B shows different views of a bronchoscope system. The user console 231 may be mounted to the robotic support system 210. Alternatively or in addition to, the user console or a portion of the user console (e.g., treatment interface module) may be mounted to a separate mobile cart.

Robotic Endoluminal Platform

In one aspect, a robotic endoluminal platform is provided. In some cases, the robotic endoluminal platform may be a bronchoscopy platform. The platform may be configured to perform one or more operations consistent with the method described in FIG. 1. FIGS. 3-7 show various examples of a robotic endoluminal platform and its components or subsystems, in accordance with some embodiments of the invention. In some embodiments, the platform may comprise a robotic bronchoscopy system and one or more subsystems that can be used in combination with the robotic bronchoscopy system of the present disclosure.

Figure 3:
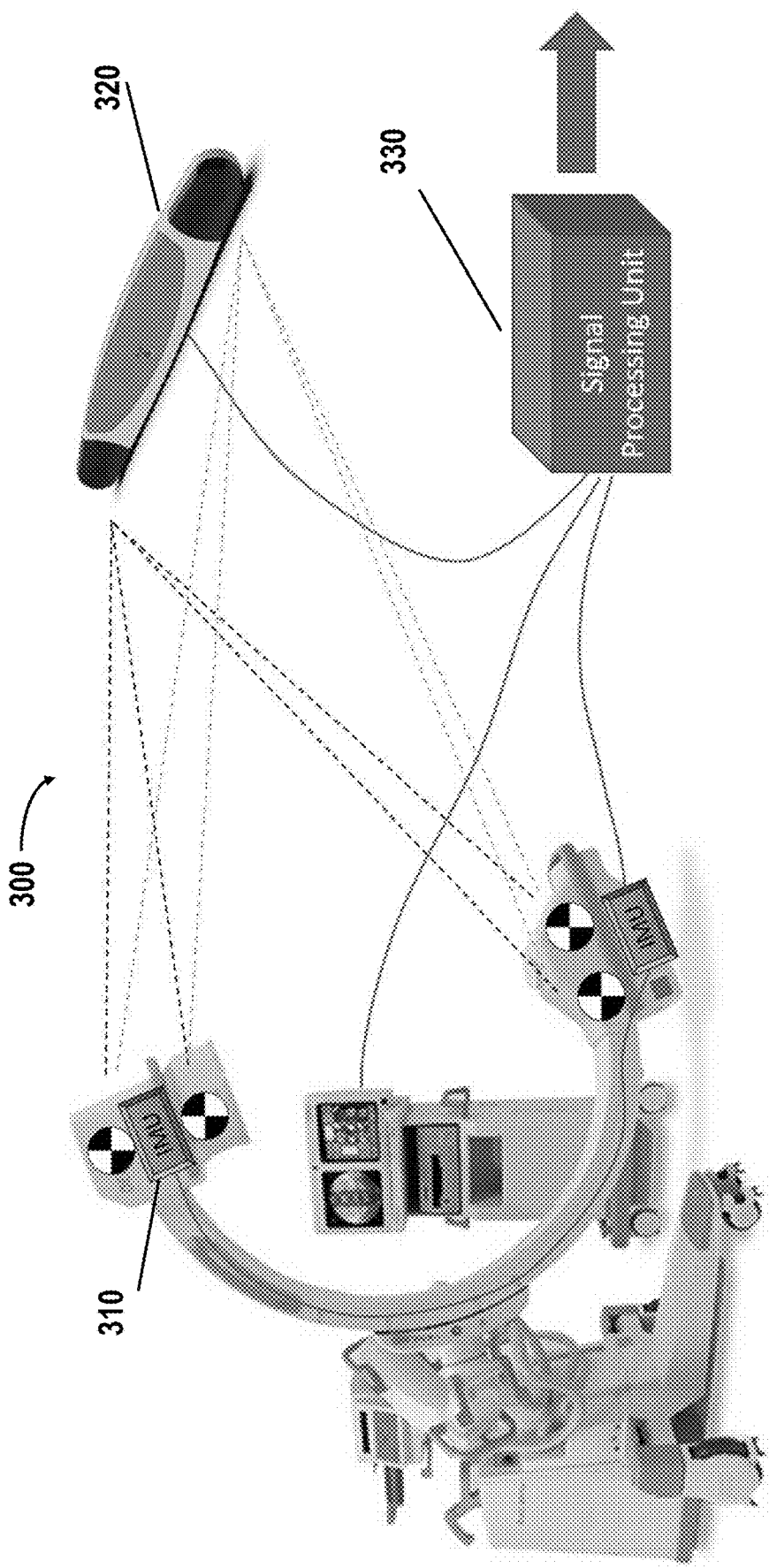
FIG. 3 shows an example of a fluoroscopy (tomosynthesis) imaging system.
Figure 4:
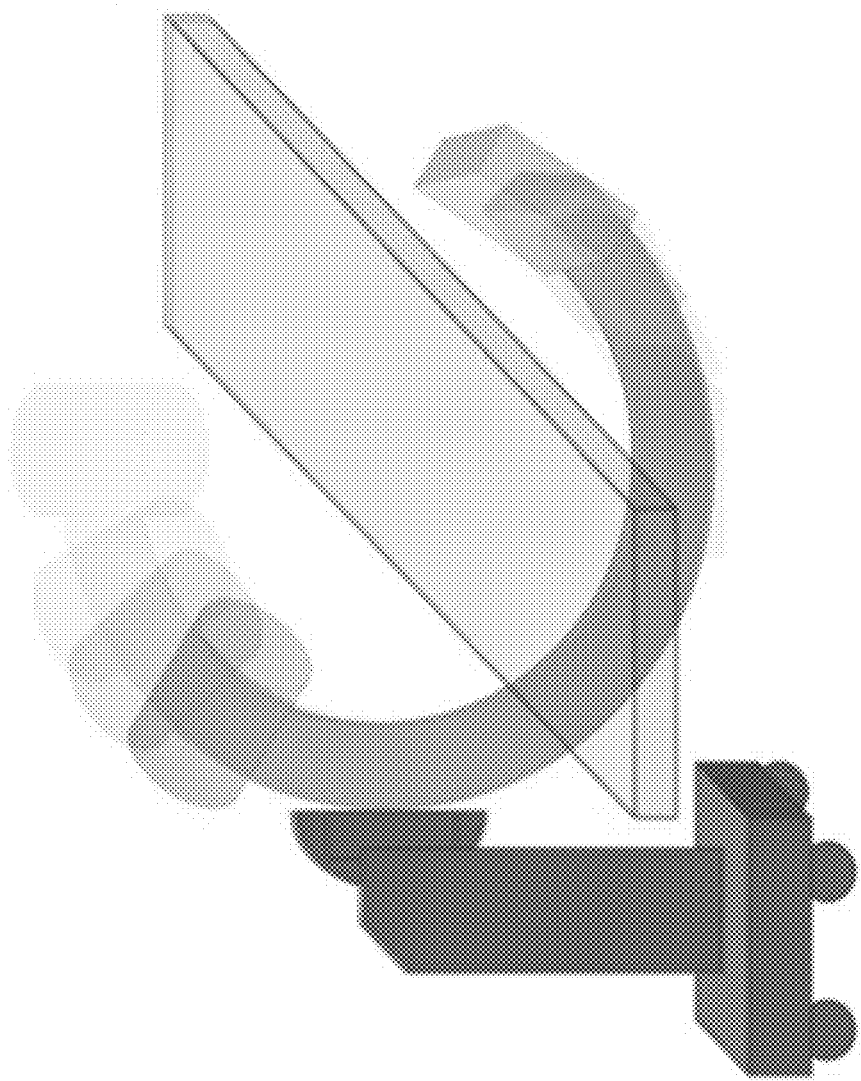
FIG. 4 shows a C-arm fluoroscopy (tomosynthesis) imaging system in different (rotation) poses while taking images of a subject.

In some embodiments, the one or more subsystems may include imaging systems such as a fluoroscopy (tomosynthesis) imaging system for providing real-time imaging of a target site (e.g., comprising lesion). FIG. 3 shows an example of a fluoroscopy (tomosynthesis) imaging system 300. For example, the fluoroscopy (tomosynthesis) imaging system may perform accurate lesion location tracking or verification before or during surgical procedure as described in FIG. 1. In some cases, lesion location may be tracked based on location data about the fluoroscopy (tomosynthesis) imaging system/station (e.g., C arm) and image data captured by the fluoroscopy (tomosynthesis) imaging system. The lesion location may be registered with the coordinate frame of the robotic bronchoscopy system. The location or motion of the fluoroscopy (tomosynthesis) imaging system may be measured using any suitable motion/location sensors 310 such as inertial measurement units (IMUs)), one or more gyroscopes, velocity sensors, accelerometers, magnetometers, location sensors (e.g., global positioning system (GPS) sensors), vision sensors (e.g., imaging devices capable of detecting visible, infrared, or ultraviolet light, such as cameras), proximity or range sensors (e.g., ultrasonic sensors, lidar, time-of-flight or depth cameras), altitude sensors, attitude sensors (e.g., compasses) and/or field sensors (e.g., magnetometers, electromagnetic sensors, radio sensors). The one or more sensors for tracking the motion and location of the fluoroscopy (tomosynthesis) imaging station may be disposed on the imaging station or be located remotely from the imaging station, such as a wall-mounted camera 320. FIG. 4 shows a C-arm fluoroscopy (tomosynthesis) imaging system in different (rotation) poses while taking images of a subject. The various poses may be captured by the one or more sensors as described above.

In some embodiments, a location of lesion may be segmented in the image data captured by the fluoroscopy (tomosynthesis) imaging system with aid of a signal processing unit 330. One or more processors of the signal processing unit may be configured to further overlay treatment locations (e.g., lesion) on the real-time fluoroscopic image/video. For example, the processing unit may be configured to generate an augmented layer comprising augmented information such as the location of the treatment location or target site. In some cases, the augmented layer may also comprise graphical marker indicating a path to this target site. The augmented layer may be a substantially transparent image layer comprising one or more graphical elements (e.g., box, arrow, etc). The augmented layer may be superposed onto the optical view of the optical images or video stream captured by the fluoroscopy (tomosynthesis) imaging system, and/or displayed on the display device. The transparency of the augmented layer allows the optical image to be viewed by a user with graphical elements overlay on top of. In some cases, both the segmented lesion images and an optimum path for navigation of the elongate member to reach the lesion may be overlaid onto the real time tomosynthesis images. This may allow operators or users to visualize the accurate location of the lesion as well as a planned path of the bronchoscope movement. In some cases, the segmented and reconstructed images (e.g. CT images as described elsewhere) provided prior to the operation of the systems described herein may be overlaid on the real time images.

In some embodiments, the one or more subsystems of the platform may comprise a navigation and localization subsystem. The navigation and localization subsystem may be configured to construct a virtual airway model based on the pre-operative image (e.g., pre-op CT image or tomosynthesis). The navigation and localization subsystem may be configured to identify the segmented lesion location in the 3D rendered airway model and based on the location of the lesion, the navigation and localization subsystem may generate an optimal path from the main bronchi to the lesions with a recommended approaching angle towards the lesion for performing surgical procedures (e.g., biopsy).

At a registration step before driving the bronchoscope to the target site, the system may align the rendered virtual view of the airways to the patient airways. Image registration may consist of a single registration step or a combination of a single registration step and real-time sensory updates to registration information. The registration process may include finding a transformation that aligns an object (e.g., airway model, anatomical site) between different coordinate systems (e.g., EM sensor coordinates and patient 3D model coordinates based on pre-operative CT imaging). Details about the registration are described later herein.

Once registered, all airways may be aligned to the pre-operative rendered airways. During robotic bronchoscope driving towards the target site, the location of the bronchoscope inside the airways may be tracked and displayed. In some cases, location of the bronchoscope with respect to the airways may be tracked using positioning sensors. Other types of sensors (e.g. camera) can also be used instead of or in conjunction with the positioning sensors using sensor fusion techniques. Positioning sensors such as electromagnetic (EM) sensors may be embedded at the distal tip of the catheter and an EM field generator may be positioned next to the patient torso during procedure. The EM field generator may locate the EM sensor position in 3D space or may locate the EM sensor position and orientation in 5D or 6D space. This may provide a visual guide to an operator when driving the bronchoscope towards the target site.

In real-time EM tracking, the EM sensor comprising of one or more sensor coils embedded in one or more locations and orientations in the medical instrument (e.g., tip of the endoscopic tool) measures the variation in the EM field created by one or more static EM field generators positioned at a location close to a patient. The location information detected by the EM sensors is stored as EM data. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively registered to the patient anatomy (e.g., 3D model) in order to determine the registration transformation that aligns a single location in the coordinate system with a position in the pre-operative model of the patient's anatomy.

Figure 5:
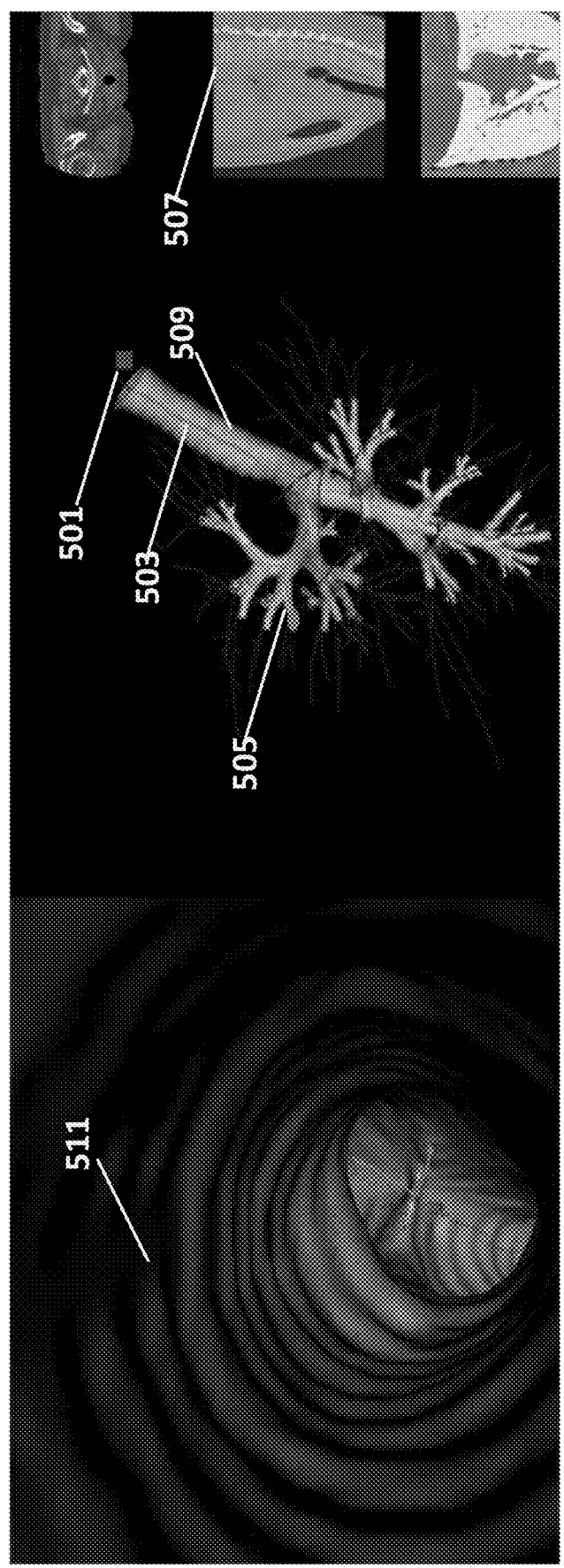
FIG. 5 shows an example of a user interface for visualizing a virtual airway overlaid with an optimal path, location of the tip of the catheter, and lesion location.

FIG. 5 shows an example of a user interface for visualizing a virtual airway 509 overlaid with an optimal path 503, location of the tip of the catheter 501, and lesion location 505. In this example, the location of the tip of the catheter is displayed in real-time relative to the virtual airway model 509 thereby providing visual guidance. As shown in the example of FIG. 5, during robotic bronchoscope driving, the optimal path 503 may be displayed and overlaid onto the virtual airway model. As described above, the virtual airway model may be constructed based on the real-time fluoroscopic image/video (and location data of the imaging system). In some cases, a view of the real-time fluoroscopic image/video 507 may also be displayed on the graphical user interface. In some cases, users may also be permitted to access the camera view or image/video 511 captured by the bronchoscope in real time.

In some embodiments, the one or more subsystems of the platform may comprise one or more treatment subsystems such as manual or robotic instruments (e.g., biopsy needles, biopsy forceps, biopsy brushes) and/or manual or robotic therapeutical instruments (e.g., RF ablation instrument, Cryo instrument, Microwave instrument, and the like).

Conventional cone beam CT machines may have the emitter and receiver panel on the same mechanical structure with a C shape or O shape. The connection between emitter and receiver panel can cause the cone beam CT to be large in size. This oversize design poses limitations on the use case and takes a lot of space in rather tight operating room.

Described herein, is a design to decouple the mechanical connection between the emitter and the receiver panel. FIG. 6 shows an example of a portable robotic cone beam CT. The emitter and receiver panel can be mounted on two separate robot arms separately, as shown in the example of FIG. 6. When in use, the two robots can move in the same coordinate system. A control algorithm may ensure that the two robots are moving in a synchronous motion.

In addition, for patients gating motion, i.e. breathing, additional external sensors—i.e. IMU, EM, or image sensors—can be added to track the motion of the patient. The position changes in patient can be tracked using sensors such as IMU, EM, or image sensors. The sensory signals can be used to command the two robot arms. In some cases, either or both of the robot arms can be moving to track the patient motions, which essentially make the emitter and receiver stationary to the patient motion for the region of interest (ROI) when tracking. The ROI may comprise a target site or a target location that can be determined automatically by the system or manually by a physician. The tracking can also be done using other mechanisms such as but not limited to external camera and one or a plurality of trackers on the patient body.

It should be understood by the person skilled in the art that cone beam CT is a nonlimiting example. The design described herein may be used for other imaging modalities such as a fluoroscopic machine, classic CT machine, and MRI machine.

Auto Registration Algorithm

The present disclosure provides an improved auto registration algorithm that can increase registration accuracy while reducing the registration time. The provided auto registration algorithm may beneficially allow for minimal user interaction, and capable of establishing transformation or registration improved over the existing method. Additionally, the provided auto registration algorithm may allow for algorithm updates on-the-fly to adapt to real time conditions (e.g., auto update of registration based on real-time detected registration error) that increase registration accuracy as the device being driven inside the subject body.

Figure 7:
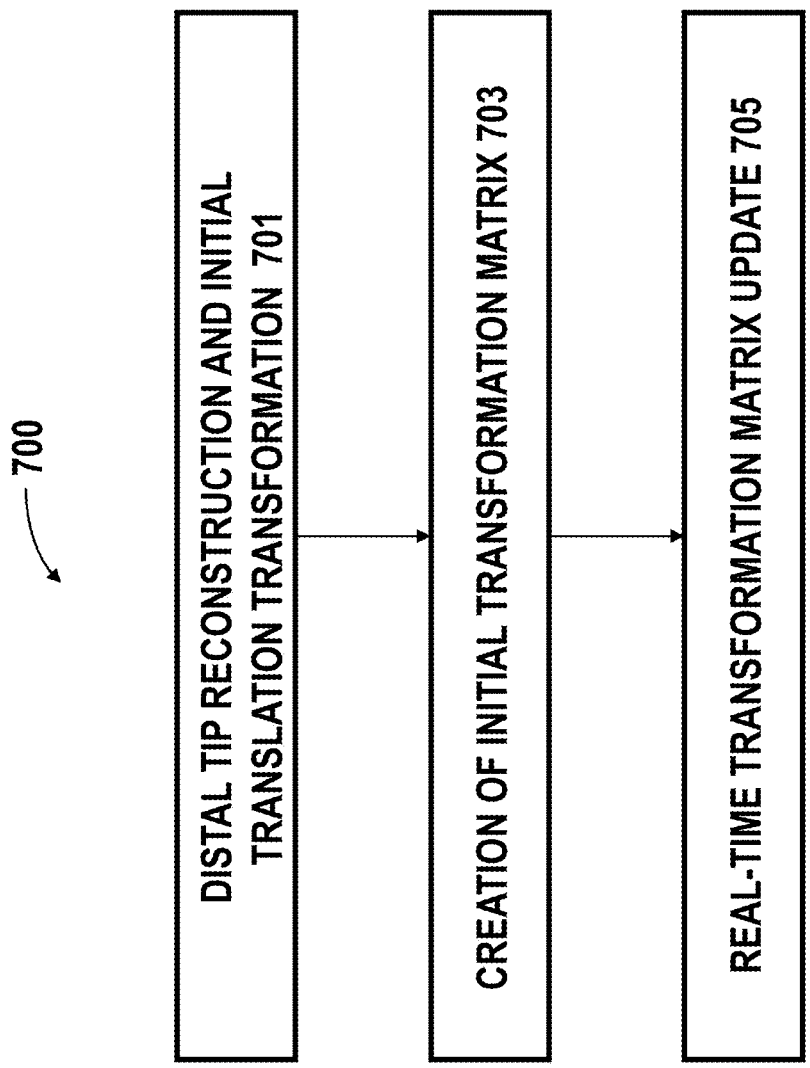
FIG. 7 schematically shows an example of an auto registration method, in accordance with some embodiments of the invention.

In some embodiments, the auto registration algorithm may comprise or can be implemented in three stages. FIG. 7 schematically shows an example of an auto registration method 700, in accordance with some embodiments of the invention. The auto registration method may include one or more algorithms to update the registration information in real-time without user input. The auto registration algorithm may also include one or more algorithms for increasing registration accuracy by identifying an optimal registration/transformation matrix and leveraging the temporal information.

As described above, an EM sensor may be coupled to a distal end of the endoscope in order to track its location within the EM field. The EM field is stationary relative to the EM field generator, and a coordinate frame of a 3D model of the luminal network (e.g., CT space) can be mapped to a coordinate frame of the EM field. As shown in FIG. 7, the auto registration method 700 may comprise a first stage which may be an initial data collection phase 701. The initial data collection phase may comprise reconstructing the distal tip of the catheter and perform an initial translation transformation.

The initial data collection phase 701 may register the EM sensor orientation to the distal tip orientation. This may establish an association between the robotic endoscopic apparatus space and the location sensor space. For example, electromagnetic coils located on the distal end may be used with the electromagnetic tracking system to detect the position and orientation of the distal tip of the catheter while it is disposed within an anatomical system (e.g., anatomical luminal network). In some embodiments, the coils may be angled to provide sensitivity to electromagnetic fields along different axes, giving the disclosed navigational systems the ability to measure a full 6 degrees of freedom: three positional and three angular. The orientation/location of the EM field generator may be unknown, and the initial data collection phase may register the EM sensor orientation (e.g., Z-axis of the EM coordinate frames) to the distal tip orientation (e.g., catheter tip Z-axis) using the collected sensor data.

During the first phase, sensor data (e.g., EM sensor data) may be collected to register the magnetic field generator's z-axis to the z-axis of the catheter tip. This may allow for flexibility in placing the magnetic field generator without a pre-known location and orientation. The sensor data may include stream data collected when the catheter is driven in a known direction. The stream data may comprise a variety of types of data including, without limitation: time series data such as spatio-temporal point measurements generated by the EM sensor. In some cases, the time series data may be collected when the catheter is driven in a known direction that may or may not be inside a patient body. For example, the EM sensor data points may be collected when the distal tip is placed inside the subject such as the bronchus or trachea and travels along a known direction. In some cases, the z-axis of the catheter tip and EM orientation may be calibrated during assembly or manufacture. In some cases, the z-axis of the catheter tip may be obtained from the robotic data when driving the catheter tip in a known direction or with aid of the CT imaging or other real-time imaging techniques. An initial translational transformation between the catheter tip and the EM field may be obtained. Such translational and rotational transformation may be continuously refined and modified during the first phase as more incoming sensor data are collected. In some cases, translational homogeneous transformation in the first phase may be updated and refined until a threshold is met. The threshold may be an accuracy threshold indicating an accuracy has been met. Alternatively or in addition to, the updates may be continuously performed (e.g., an error may be calculated at each time interval) and the update may be stopped when tomosynthesis targeting is in progress In some cases, the collected sensor data may also provide registration in terms of translational transformation between the CT space (e.g., tissue) and the EM space (e.g., catheter). For example, a registration transformation between the EM field and the patient model (e.g., coordinate frames of the luminal network model) may be identified. This translational transformation in the second phase may include an initial translation transformation matrix which may be later refined in the final phase as described later herein.

The second phase 703 of the registration method may comprise creating an association between the EM space and model (e.g., CT) space. During the second phase, an initial transformation matrix between the EM space and CT space may be generated based at least in part on the translation information generated in the first phase and real-time sensor data. In some cases, data points (e.g., EM data) utilized in the second phase may be collected when the catheter is navigating inside the trachea and/or a child branch along a predefined navigation path. The predefined navigation path may be defined in the CT space. As described elsewhere herein, EM data may include information about the orientation, position and error data. The CT space or the coordinate frame of the anatomical model may be generated in a pre-operative procedure or during a surgical operation. Such sensor data points may be used to establish a plane in space, and establish a set of associations between the EM space and CT space based on a set of directional distances traveled (e.g., both orientation and length) in the EM space and CT space respectively. The set of associations may be generated based at least in part on the time series data such as the spatio-temporal data points generated by the EM sensor.

In some cases, the set of associations may be processed to identify an optimal transformation matrix. For example, a best fit for the EM curve (e.g., point clouds in EM space) to the established CT curve (e.g., point cloud in CT space) in 3D space may be determined to identify the optimal transformation matrix. For example, the provided auto registration method may employ a modified version of Iterative closest points (ICP) algorithm with nearest neighbors and singular value decomposition to iterate the calculations toward the optimal solution. It should be noted other algorithms or variations suitable for identifying an optimal fit may be adopted.

Figure 8:
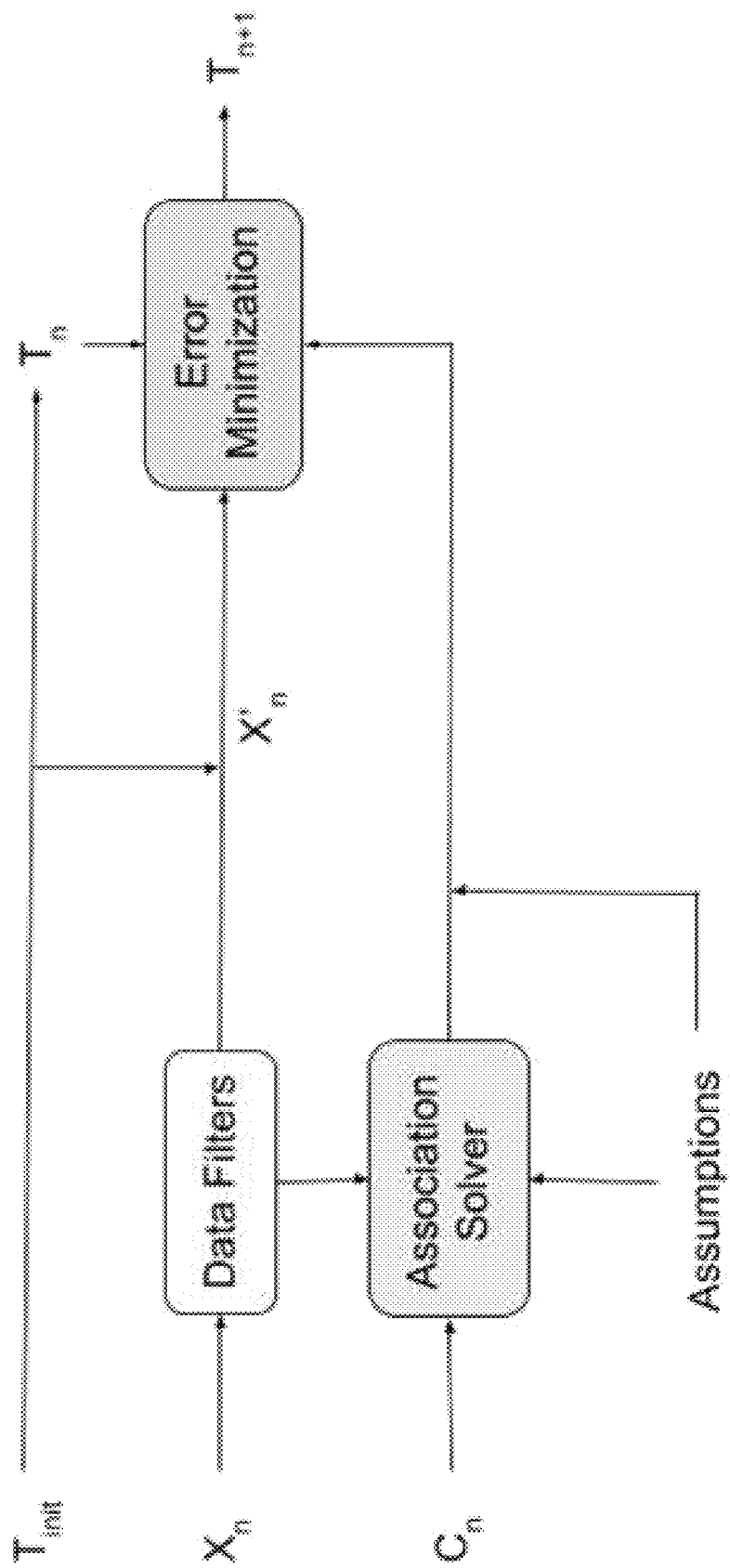
FIG. 8 shows an example of a customized Iterative closest points (ICP) algorithm.

FIG. 8 shows an example of a customized Iterative closest points (ICP) algorithm for generating an initial transformation between two data point clouds (e.g., EM domain point cloud and CT domain point cloud). ICP is an iterative algorithm that alternates between determining, based on the current transformation estimate, the nearest neighbors (NN) of every point of one shape, and updating the estimate based on the NN. The association solver may receive the computed set of associations between the two sets of data point clouds in the CT space and EM space (e.g., Cn, Xn) and is executed to obtain the transformation that best match the set of associations. As an example, the set of associations may be calculated using a k-nearest neighbors (k-NN) algorithm. The best fit transform may be calculated using singular value decomposition during the error minimization step. The assumptions (e.g., proximity assumption) may be modified to soft lock the transformation translation and rotation to good initial values.

Figure 9:
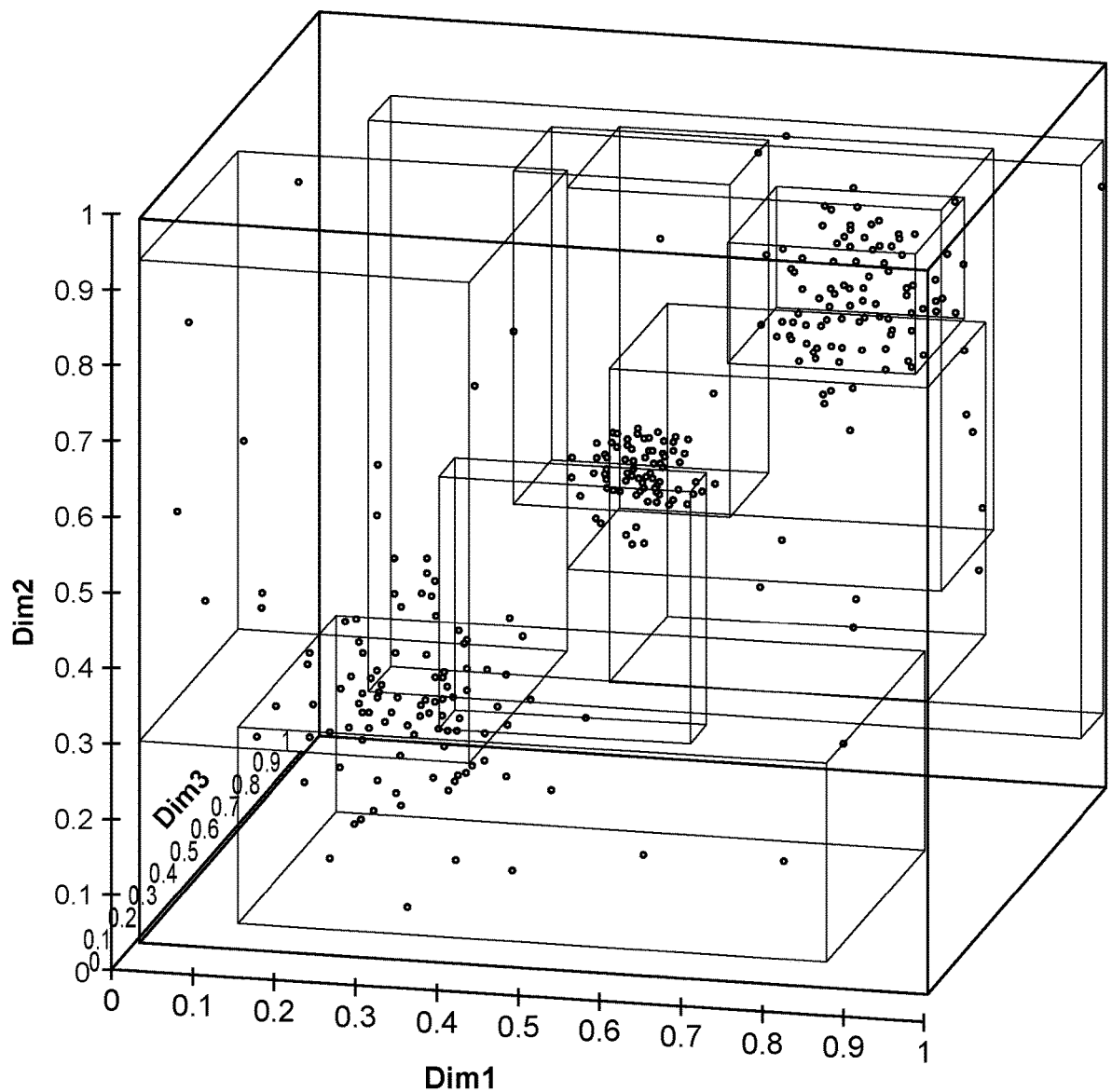
FIG. 9 shows an example of a classification result.
Figure 10:
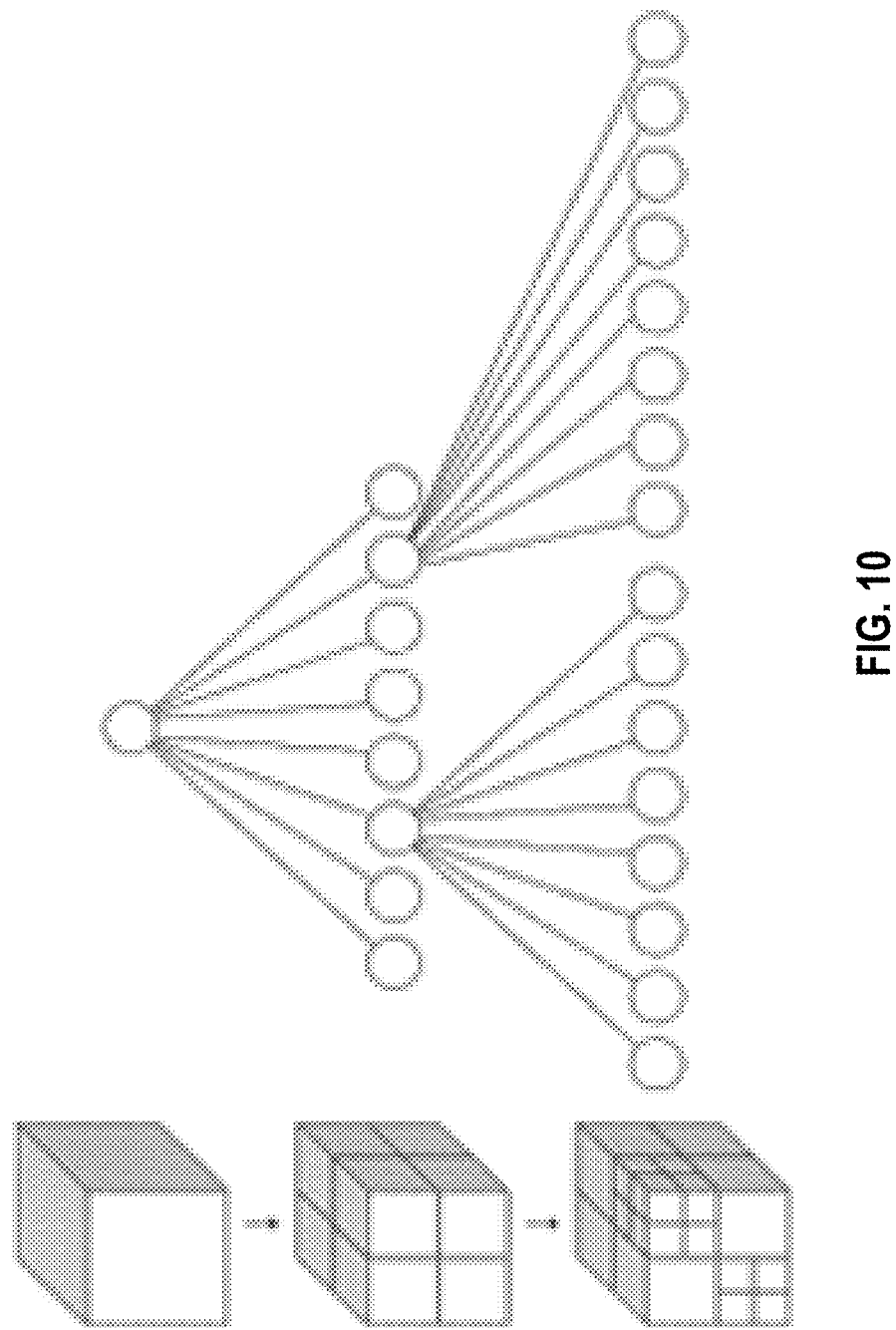
FIG. 10 shows an example of the data structure (spatial data structure). The specialized data structure may be k-d trees or octrees data structure.

An example of the classification result is shown in FIG. 9. The provided method may further improve the k-NN algorithm performance to reduce computation time by utilizing a specialized data structure. FIG. 10 shows an example of the data structure (spatial data structure). The specialized data structure may be k-d trees or octrees data structure. The k-d trees or octrees data structure can allow for efficient implementations of NNS due to their regular partitioning of the search space and the high branching factor, coordinate queries are fast. Other data structures suitable for shape registration and storage efficiency can also be utilized.

Referring back to FIG. 8, the error minimization operation may include using singular value decomposition to calculate the best fit transform. For example, the singular value decomposition may be applied to a set of associations to calculate the best transformation. The singular value decomposition method may be used to calculate a solution to a total least squares minimization problem.

It should be noted that the abovementioned algorithms can be modified or substituted by other algorithms. For example, a coherent point drift algorithm may be employed to identify the best fit transformation based on probability rather than rigid point locations. The algorithm may scale up a point cloud (and/or deform the point cloud using probabilistic convergence) while rotating it so that calculated features, usually centroids, traverse a probabilistic optimization surface until alignment with the other point cloud. The coherent point drift algorithm or other probability based algorithm may reduce the impact of noise in a dataset.

Referring back to FIG. 7, the third phase 705 of the auto registration algorithm may comprise updating the initial registration/transformation generated in the second phase. In some embodiments, the update method may include a weak real-time update and a strong real-time update to the initial transformation. The weak real-time update may also be referred to as fast interval update, the strong real-time update may also be referred to as slow interval update which are used interchangeably throughout the specification. The update may be performed using real-time data without user intervention. In some cases, the update may utilize collected real-time EM sensor data from a large point cloud. In some cases, a subset of data points from the large point cloud may be selected/sampled for calculating an error and determining whether an update is needed based on the error.

In some cases, the update method may include a weak and a strong real-time update to the initial transformation. For example, the update method may include a fast interval refine step and a slow interval recalculate step. In some cases, after each update, the error may be recalculated and the transformation matrix may be updated when the error decreases.

The fast interval refine operation (e.g., fast interval update) may involve randomly sampling a subset of data points from the large point cloud (e.g., data points collected in the third phase). Next, the current transformation and the nearest neighbors algorithm may be applied to the sampled set to create a set of associations. The set of associations may be combined with the set of associations calculated in the second phase to create a final point cloud. The final point cloud data may be fed into the modified ICP algorithm as described in the second phase to generate an updated transformation thereby refining the current transformation.

The slow interval recalculate operation may comprise a similar update operation as described above while using only the nearest neighbor algorithm without utilizing the initial transformation information or the set of associations generated in the second phase. For example, a set of associations may be calculated by applying the nearest neighbor algorithm to the sensor data collected in the third phase and the transformation matrix may be updated using only the set of associations without information from the second phase. In some cases, the subset of data may be randomly sampled from a large dataset. Alternatively or additionally, the subset of data may be selected based on distance. For example, a distance based temporal filter may be used to sample uniformly distributed points along a temporal path and select such points for the update calculation. The distance used to filter may be based on the CT scan and/or patient anatomy.

Such slow interval recalculate operation (i.e., strong update) may be performed on a greater time/points interval because it may result in a "jump" to the next local minimum. In some cases, the slow recalculation may be performed at fixed intervals (e.g., time interval, a pre-determined number of data points, etc.). In some cases, the slow recalculation may be triggered when the update error values start converging, signaling that a local or global minimum is reached. As the initial transformation is constantly being refined by the weak update (i.e., fast interval recalculation), and the iterations of the ICP algorithm, the "jump" can be ensured to be a desired step or in the correct direction. Combing the weak update (e.g., fast interval refine) and the strong update as well as performing the weak updates more frequently than the strong update may beneficially ensure that the "jump" is in the correct direction, as a refine step increases the distance to incorrect local minimums while decreasing the distance to the global minimum.

The random sampling of the data points in the update phase (e.g., fast interval update) may also beneficially prevent overfitting. Overfitting may occur due to noisy data and fitting a cylinder of data to a single line. The random sampling may provide the capability of finding and refining a general solution instead of jumping from a local minimum to another local minimum thereby allowing for a smoothly traverse the error surface and improving the registration accuracy and stability. Random sampling of the data points may also indirectly weight the initial associations into the estimated associations (calculated in the fast interval recalculation). Data with high accuracy is calculated in the second phase, and it is desirable to weight this calculation more than the nearest neighbor calculation, due to the complicated structure and small gaps between periphery airways. Radom data sampling in the update step may further avoid getting stuck in a local minimum which can halt the entire registration progress. Hitting a local minimum may be unavoidable, primarily because even if a global solution is found at iteration x, iteration x+1 may add data, causing the previous transformation to become a local minimum. Random sampling may beneficially smooth the iterations and the error calculation.

In some embodiments, the auto registration algorithm may also employ preprocessing algorithm to preprocess collected sensor data to improve the performance. In some cases, Ramer-Douglas-Peucker algorithm may be used to preprocess a large dataset of time series data between two location points. The algorithm recursively finds points that preserve the overall dataset shape while simplifying the path. In some cases, algorithms such as exponential smoothing may be used to remove noise from the dataset while preserving small fluctuations in the curve. In another example, filters such as alpha-beta filtering may be utilized to remove noise from a dataset. In some cases, a distance based temporal filter may be used to select the subset of data as described above.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for navigating a robotic endoscopic apparatus, the method comprising:
   (a) generate a first transformation between an orientation of the robotic endoscopic apparatus and an orientation of a location sensor based at least in part on a first set of sensor data collected using the location sensor;
   (b) generating a second transformation between a coordinate frame of the robotic endoscopic apparatus and a coordinate frame of a model representing an anatomical luminal network based at least in part on the first transformation and a second set of sensor data; and
   (c) updating, based at least in part on a third set of sensor data, the second transformation using an updating algorithm, wherein the updating algorithm comprises a fast interval recalculation operation and a slow interval recalculation operation and wherein the fast interval recalculation operation comprises (i) calculating a first set of associations using a subset of data sampled from the third set of sensor data and (ii) combining the first set of associations with a second set of associations calculated for generating the second transformation in (b).

2. The method of claim 1, further comprising calculating a point cloud using the combined first and second set of associations.

3. The method of claim 1, wherein the slow interval recalculation operation comprises a nearest neighbor algorithm.

4. The method of claim 1, wherein the slow interval recalculation operation comprises updating the second transformation using only the third set of sensor data.

5. The method of claim 1, wherein the location sensor is an electromagnetic sensor.

6. The method of claim 1, wherein the coordinate frame of the model representing an anatomical luminal network is generated using a pre-operative imaging system.

7. The method of claim 1, wherein the robotic endoscopic apparatus comprises a disposable catheter assembly.

8. The method of claim 1, wherein the location sensor is located at a distal tip of the robotic endoscopic apparatus.

9. A system for navigating a robotic endoscopic apparatus comprising:
- a location sensor coupled to the robotic endoscopic apparatus; and
- one or more processors in communication with the location sensor and the robotic endoscopic apparatus and configured to execute a set of instructions to cause the system to:
  - (a) generate a first transformation between an orientation of the robotic endoscopic apparatus and an orientation of the location sensor based at least in part on a first set of sensor data collected using the location sensor;
  - (b) generate a second transformation between a coordinate frame of the robotic endoscopic apparatus and a coordinate frame of a model representing an anatomical luminal network based at least in part on the first transformation and a second set of sensor data; and
  - (c) update, based at least in part on a third set of sensor data, the second transformation using an updating algorithm, wherein the updating algorithm comprises a fast interval recalculation operation and a slow interval recalculation operation and wherein the fast interval recalculation operation comprises (i) calculating a first set of associations using a subset of data sampled from the third set of sensor data and (ii) combining the first set of associations with a second set of associations calculated for generating the second transformation in (b).

10. The system of claim 9, wherein the fast interval recalculation operation further comprises calculating a point cloud using the combined first and second set of associations.

11. The system of claim 9, wherein the slow interval recalculation operation comprises a nearest neighbor algorithm.

12. The system of claim 9, wherein the slow interval recalculation operation comprises updating the second transformation using only the third set of sensor data.

13. The system of claim 9, wherein the location sensor is an electromagnetic sensor.

14. The system of claim 9, wherein the coordinate frame of the model representing the anatomical luminal network is generated using a pre-operative imaging system.

15. The system of claim 9, wherein the robotic endoscopic apparatus comprises a disposable catheter assembly.

16. The system of claim 9, wherein the location sensor is located at a distal tip of the robotic endoscopic apparatus.

* * * * *